United States Patent [19]
McGuinness

[11] Patent Number: 5,385,535
[45] Date of Patent: Jan. 31, 1995

[54] CERVICAL COLLAR

[76] Inventor: Charles McGuinness, 10 Karen Ave., Plainview, N.Y. 11803

[21] Appl. No.: 128,307

[22] Filed: Sep. 28, 1993

[51] Int. Cl.⁶ ................................................ A61F 5/00
[52] U.S. Cl. .............................. 602/18; 128/DIG. 23
[58] Field of Search ............... 128/845, 846, 869, 870, 128/DIG. 23; 602/18, 19; 5/630; 606/130

[56] References Cited

U.S. PATENT DOCUMENTS

| | | | |
|---|---|---|---|
| 1,930,440 | 10/1933 | Longfellow | 602/18 |
| 3,364,926 | 1/1968 | Alderson | 602/18 |
| 3,507,273 | 4/1970 | Yellin | 602/18 |
| 3,724,452 | 4/1973 | Nitschke . | |
| 4,793,334 | 12/1988 | McGuinness | 602/18 |
| 4,807,605 | 2/1989 | Mattingly | 602/19 |
| 5,005,563 | 4/1991 | Veale | 602/18 |
| 5,010,881 | 4/1991 | Boudreau | 602/19 |
| 5,088,482 | 2/1992 | McGuinness | 602/18 |
| 5,171,296 | 12/1992 | Herman | 602/18 |

FOREIGN PATENT DOCUMENTS 2233900  1/1991  United Kingdom .

OTHER PUBLICATIONS

Arch. Phys. Med. Rehabil., vol. 73, Dec., 1992, pp. 573–575.

*Primary Examiner*—Michael A. Brown
*Attorney, Agent, or Firm*—Galgano & Burke

[57] ABSTRACT

A cervical collar includes a generally annular support brace which, in use, is receivable about and circumferentially surrounds a wearer's neck and is generally supportable on the wearer's shoulders and upper torso. The support brace includes a pair of vertically-spaced-apart, interconnected and generally horizontally-disposed, arcuate, upper and lower support members, each having a front central portion and rear opposite terminal end portions which, in use, are disposed generally adjacent to the front and rear of the wearer's neck, respectively. The support brace also has adjustable and releasable rear straps for joining the terminal end portions of the support members together. A chin support is also provided for engaging and supporting the chin of the wearer, which is mounted on the support brace.

21 Claims, 4 Drawing Sheets

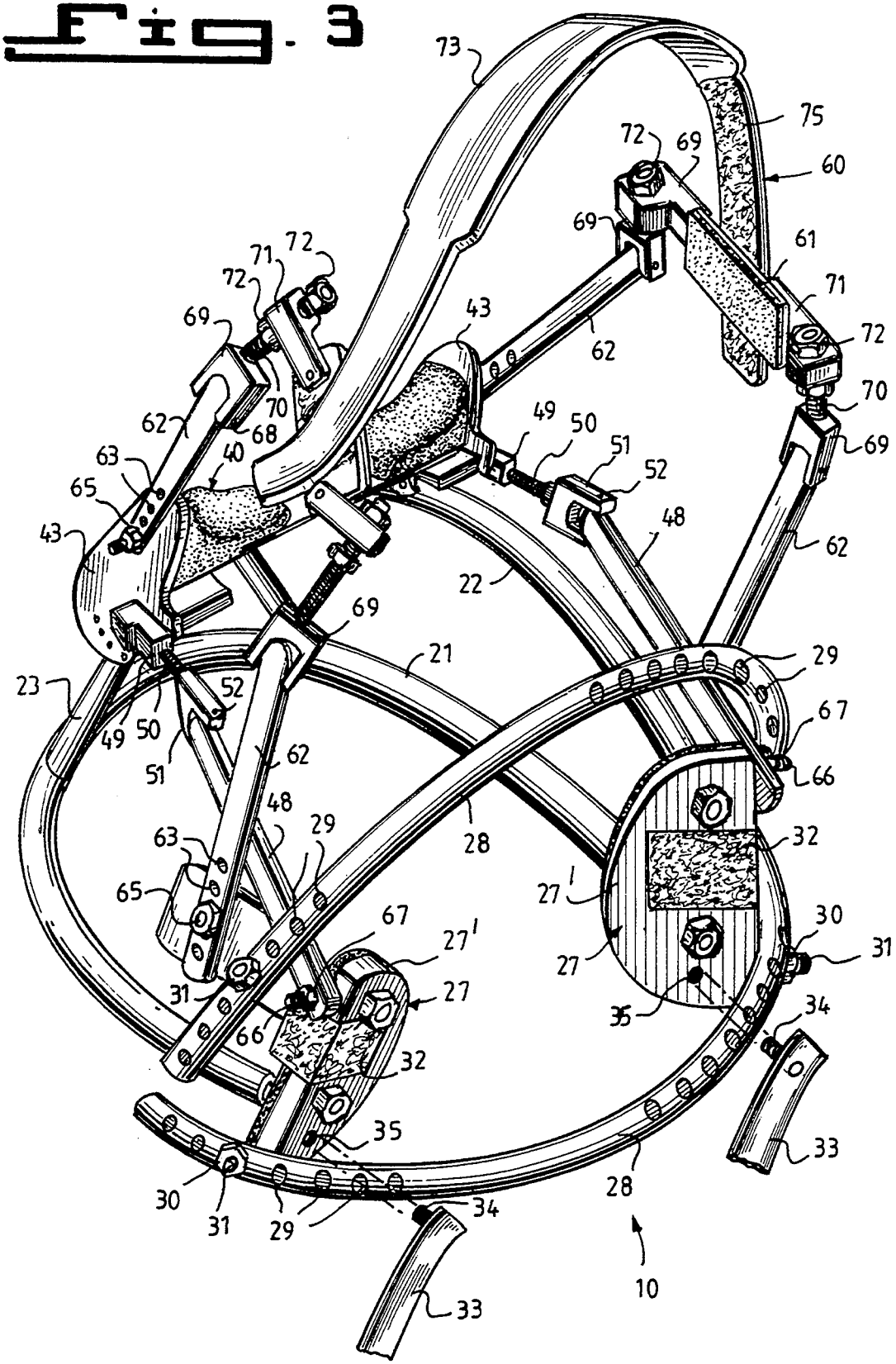

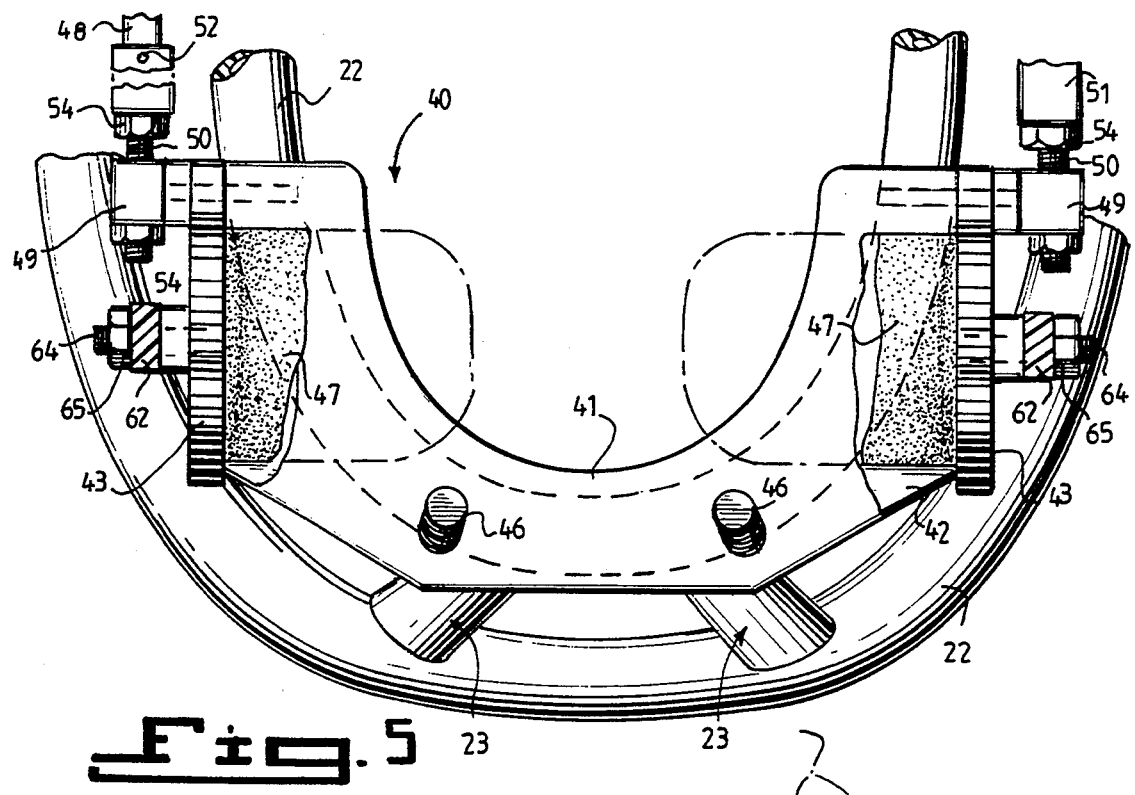
Fig. 5
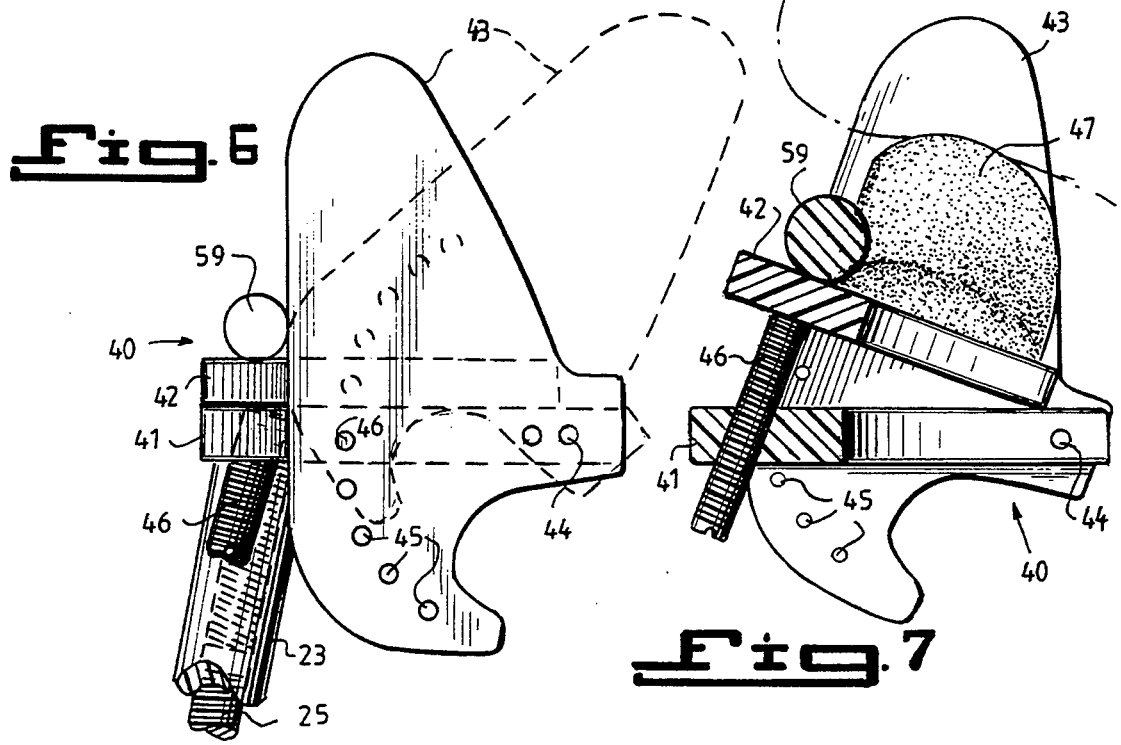
Fig. 6
Fig. 7

CERVICAL COLLAR

BACKGROUND OF THE INVENTION

The present invention relates to an improved cervical collar or brace In general, cervical collars or braces are worn to correct or ease discomfort from spinal injuries, particularly spinal injuries in the area of the neck vertebrae. In particular, cervical braces are commonly used to rectify any spinal damage caused as a result of whiplash injury.

There are a number of types of such braces. For example, one type comprises a relatively stiff collar worn around the neck, which extends between the shoulders and the jawbone and chin of the wearer. While such collars do give a certain amount of support, they do not provide for adjustment to accommodate varying lengths of different people's necks. Thus, on some they may be relatively comfortable, while on others they can cause considerable discomfort. For example, in the case of an individual with a relatively short neck, such a collar may cause the chin to be retained at a totally incorrect angle. Further, for an individual with a relatively long neck, the chin may also be supported at the wrong angle. A further problem with such collars is that they are clearly visible for all to see and, in general, are relatively unsightly. Furthermore, because they are worn completely around the neck, there is very little circulation of air between the collar and the neck. Accordingly, they tend to induce perspiration in the neck area which further leads to discomfort. Various attempts have been made to overcome the problems of such collars. Examples of such attempts are given in the following patent specifications, namely, U.S. Pat. Nos. 3,724,452, 3,945,376, 4,383,523 and 4,628,913, and UK Patent No. 2,233,900. In general, these cervical braces comprise a harness for mounting on the torso of the body, and a chin support member for supporting the chin of the wearer. The chin support member is mounted on a support bar which is adjustable upwardly and downwardly to accommodate wearers with different lengths of neck. However, while these devices partly overcome the problems of stiff collars in that at least the height at which the wearer's chin is supported can be adjusted, nonetheless they do not provide for the different positions which individuals chins may take up, in other words, the position of a wearer's chin front to back. Accordingly, while the chin supports may be adjusted to accommodate different heights of chins, this does not ensure that the chin support will accurately or correctly engage the wearer's chin. For example, if a wearer has a chin which projects more than normally, or a wearer has a chin which projects less than normally, then the chin support will not adequately support the wearer's chin.

Another known device is the "halo" brace. Such a device also has a harness for mounting on the torso and upright members which extend to the top of the wearer's head. A "halo" or ring is attached to the upright members which encircles the head in the forehead area. Four equally-spaced adjusting screws are installed in the halo and screwed toward the wearer's head. Depressions are made in the skull to receive the adjusting screws. The screws are tightened so as to restrict movement of the head and neck. However, the device is not very effective and, in addition, is bulky and unsightly. Furthermore, problems can develop with a single skull depression requiring total refitting of the device.

An improved cervical brace is described in U.S. Pat. No. 4,793,334. This device overcame some of the problems with cervical braces, namely, the chin support member was adjustable both up and down, as well as front to back. However, the chin support member in this device was not comfortable as it "clamped" onto the wearer's chin. In addition, although a support is provided for the wearer's occiput, it is not sufficiently adjustable. Furthermore, the two-point support member for the chin support is not stable, i.e., it is flexible in the left-right direction. In addition, it has a complex harness assembly and requires changing the settings to remove the device.

In addition, a cervical collar is disclosed in *Arch Phys. Med. Rehabil.*, Vol. 73, December 1992, p. 573-575, made of rigid polythene, anatomically shaped with a cut out piece anterolaterally for ventilation. An anterior screw allows adjustment in length to variable neck height and the posterior Velcro ® fastening allows adaptation to embrace all neck diameters. However, the device does not afford sufficient combinations of adjustability, rigidity (i.e., immobility) and ventilation for the purposes presently proposed.

In my prior patent, U.S. Pat. No. 5,088,482 (the subject matter of which is incorporated herein by reference thereto), a cervical brace is disclosed which utilizes the advantages found in U.S. Pat. No. 4,793,334, and overcomes the deficiencies in the aforementioned prior art. This patented cervical brace comprises a torso engaging member having a back portion and a front portion. The front portion in use being adjacent to the front of the torso and the rear portion, in use, being adjacent to the back of the torso. A chin support member is provided for engaging and supporting the chin of the wearer, together with mounting means including an adjustable and releasable strut and brace assembly for mounting the chin support member to the torso engaging member so that the chin support member is easily adjustable and is movable upwardly and downwardly in addition to backwardly and forwardly relative to the torso engaging member for accommodating, in use, different positions of a wearer's chin.

The present invention is directed toward an improvement of such a cervical brace or collar.

SUMMARY OF THE INVENTION

Accordingly, it is an object of the present invention to provide an improved cervical brace which comprises a chin support member for supporting a wearer's chin which can be adjusted to engage a patient's chin accurately and snugly, i.e., it is an object of the invention to provide a cervical brace in which the chin support member is adjustable not only upwardly and downwardly but also forwardly and backwardly relative to the wearer.

It is also an object of the invention to provide an improved cervical brace which, as well as supporting the chin, also adjustably supports the wearer's occiput, and thus the entire head, i.e., the head support member is adjustable upwardly, downwardly, forwardly and rearwardly.

Another object of the invention is to provide a cervical brace which can be relatively easily fitted and removed.

It is a further object of the present invention to provide such a cervical brace which provides a more comfortable fit for the wearer while, at the same time, providing the degree of immobility required of the patient's neck.

Yet a further object is to provide a cervical brace with a plurality of adjustments that can easily be made by an individual with relatively little training with the device.

It is a more particular object of the invention to provide a cervical brace which provides support by non-intrusive means, i.e., fits externally on the wearer, is X-ray transmissive and provides essentially 360° of air ventilation around the wearer's neck.

Certain of the foregoing and related objects are readily attained in a cervical collar which includes a generally annular support brace which, in use, is receivable about and circumferentially surrounds a wearer's neck and is generally supportable on the wearer's shoulders and upper torso. The support brace includes a pair of vertically-spaced-apart, interconnected and generally horizontally-disposed, arcuate, upper and lower support members each having a front central portion and a pair of rear opposite terminal end portions which, in use, are disposed generally adjacent to the front and rear of the wearer's neck, respectively, and adjustable and releasable rear strap means for joining said terminal end portions of said support members together. Chin support means are provided for engaging and supporting the chin of the wearer, as well as mounting means for adjustably mounting the chin support means on the support brace.

Preferably, the support brace includes a pair of generally vertically-extending rear struts interconnecting the rear terminal end portions of the support members and the strap means, in turn, interconnects the rear struts. Advantageously, the strap means includes at least one strap disposed over and generally above the terminal end portions of the upper support member so as to be positioned to support the back of the head of the wearer.

Most advantageously, the strap means includes a second rear strap spaced below the first strap.

In a particularly preferred embodiment of the invention, the support members comprise plastic resilient tubes, preferably made of PVC, and the strap means also comprise plastic tubes. The plastic tube straps each have a plurality of spaced-apart adjustment holes formed therethrough and the strap means includes releasable fasteners for joining the tubes via the adjustment holes to the rear struts.

Most desirably, the support brace includes a pair of generally vertically-extending, spaced-apart front struts interconnecting the front central portions of the support members. The front struts each preferably comprise a turnbuckle for adjusting the spacing between the support members.

In a further preferred embodiment, the mounting means includes means for pivotably supporting the chin support means. The means for pivotably supporting the chin support means advantageously includes a generally horizontally-disposed pivot support plate adjustably mounted on the collar support, with the chin support means being pivotably mounted on the pivot support plate.

It is especially desirable that the chin support means includes a generally horizontally-disposed chin support plate and a pair of generally vertically-disposed lateral end walls, each joined to an opposite lateral end of the chin support plate. The lateral end walls includes pivot means for pivotably mounting the lateral end walls on the pivot support plate. Releasable locking means are also provided for locking the lateral end walls and, in turn, the chin support plate at a predetermined and adjustable pivot angle with respect to the pivot support plate. Most advantageously, the lateral end walls have a plurality of spaced-apart holes formed therethrough and the pivot support plate has a pair of opposite lateral side walls, each with a threaded throughbore formed therein. The releasable locking means include a pair of threaded locking pins each of which is releasably received in one of said holes and throughbores so as to lock the lateral end walls of the chin support plate at a fixed pivot angle with respect to the pivot support plate.

In yet a further embodiment of the invention, the chin support plate and the lateral end walls have resilient chin rest means mounted thereon configured to generally conform to and provide direct support for the wearer's chin. The mounting means preferably includes adjustable-length side support braces, one end of each of which is attached to an opposite lateral end wall of the chin support means and an opposite rear strut of the support brace. Most desirably, one end of the side support braces is connected to either the rear struts or the lateral end walls via pivot means.

In a particularly preferred embodiment of the invention, the collar additionally includes a pair of head support members for engaging and supporting the occiput of the wearer and mounting means for adjustably mounting the head support members on support braces and/or the chin support means. Most desirably, the mounting means comprises two pairs of adjustable-length head support struts, one pair of each of which is connected, at their first ends, to an opposite head support member, at their opposite ends, and to one of the rear support struts and the lateral end wall of the chin support means. Preferably, the head support struts are connected to the head support member via pivot means. Most advantageously, the collar additionally includes releasable strap means connecting the pair of head support members, and the collar may additionally include strap means for connecting the support brace to the wearer's torso. Finally, it is also extremely advantageous that the annular support brace, chin support means and mounting means are fabricated from X-ray transmissive materials.

BRIEF DESCRIPTION OF THE DRAWINGS

Other objects and features of the present invention will become apparent from the following detailed description considered in connection with the accompanying drawings. It should be understood, however, that the drawings are designed for the purpose of illustration only and not as a definition of the limits of the invention.

In the drawings, wherein similar reference characters denote similar elements throughout the several views:

FIG. 3 is a rear and left side perspective view of the cervical collar;

FIG. 4 is an enlarged, fragmentarily-illustrated perspective view, in part section, of the chin support assembly and support base;

FIG. 5 is an enlarged, fragmentarily-illustrated plan view, in part section, of the chin support assembly;

FIG. 6 is a side elevational view, in part section, of the chin support assembly, showing the pivotable adjustment thereof in phantom view; and FIG. 7 is a side elevational view, in part section, of the chin support assembly pivoted to a position to support the chin of the patient, shown in phantom line.

DETAILED DESCRIPTION OF THE PREFERRED EMBODIMENT

Figure 1:
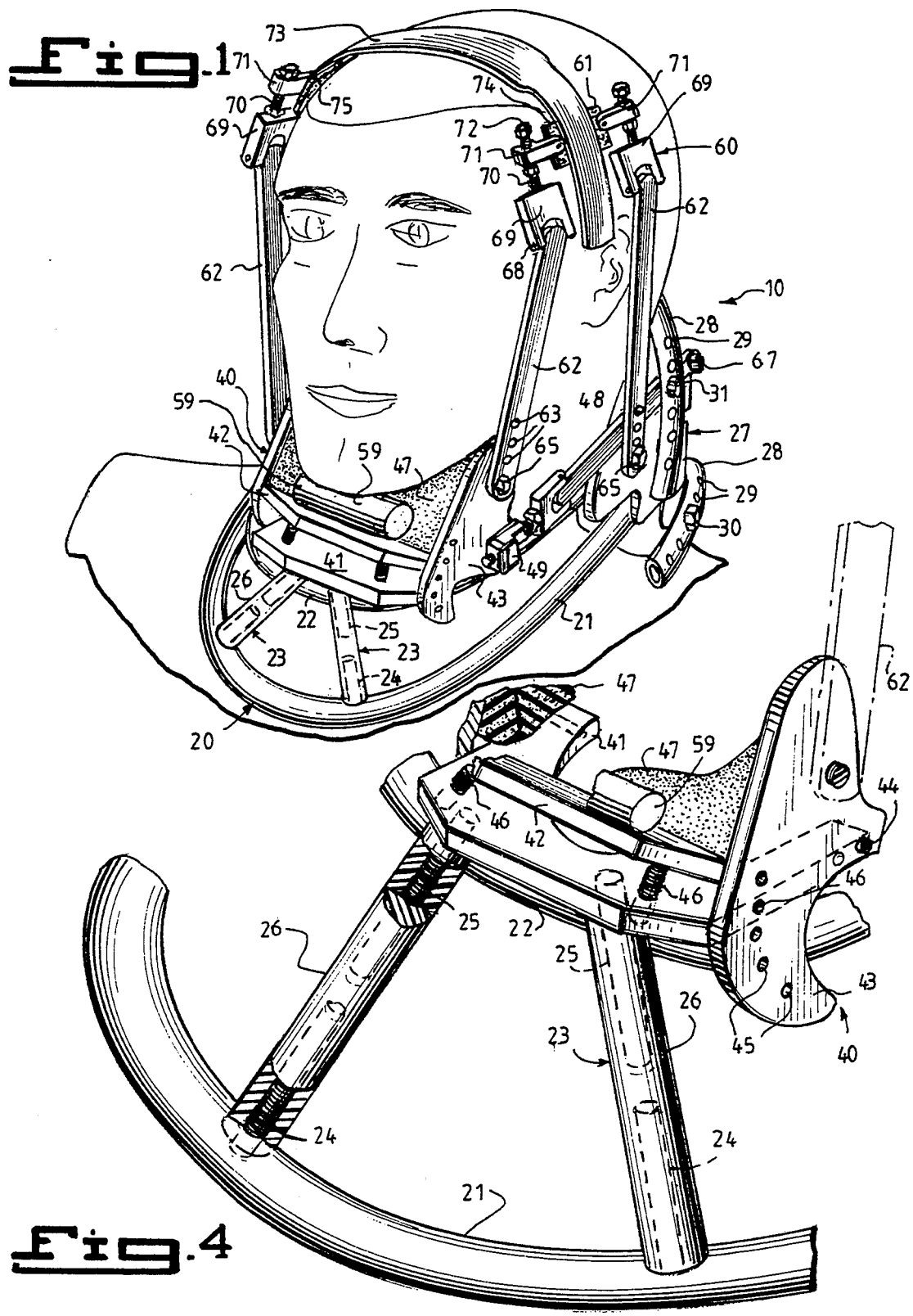
FIG. 1 is a front and left side perspective view of a cervical collar according to the invention showing the same being worn by a patient.
Figure 2:
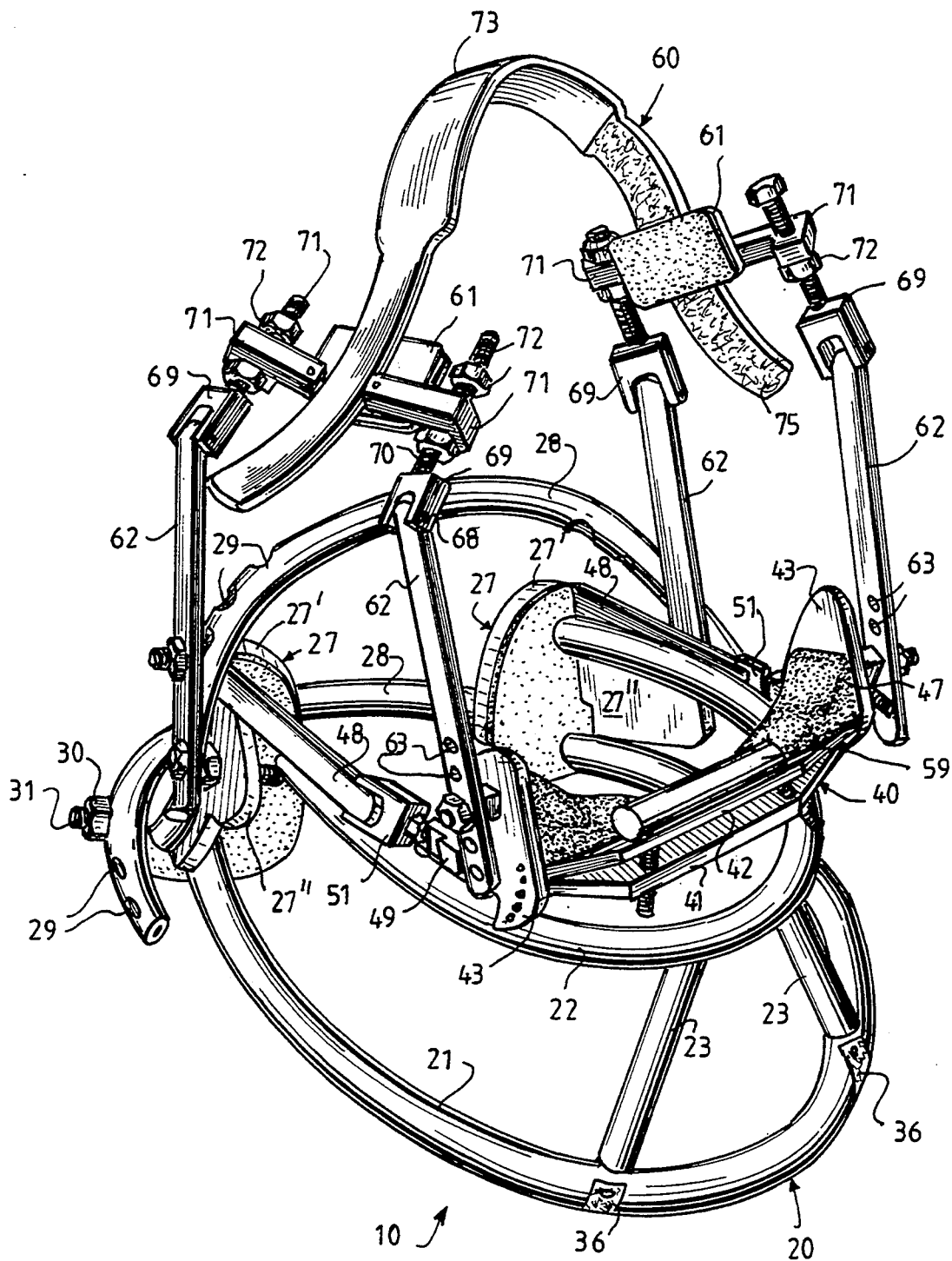
FIG. 2 is a front and right side perspective view of the cervical collar.

Turning now in detail to the drawings, and in particular to FIGS. 1–3 thereof, therein illustrated is a cervical brace according to the invention, indicated generally by reference numeral 10. The cervical collar 10 includes a generally annular support brace, generally designated 20, which, in use, is receivable about and circumferentially surrounds a wearer's neck and is generally supportable on the wearer's shoulders and upper torso. The collar further includes a chin support assembly 40 and a head support assembly 60.

The support brace 20 includes a pair of vertically spaced-apart, interconnected and generally horizontally disposed arcuate lower and upper support members 21, 22 preferably made of transparent or translucent PVC plastic tubing having an outside diameter of approximately ⅝ of an inch, an inside diameter of approximately ½ an inch and a wall thickness of approximately 3/16 of an inch. The plastic tube is approximately 20 inches in length, which, of course, can be adjusted to the general neck size desired (i.e., infant to adult). The front portions of the lower and upper support members 21, 22 are interconnected via a pair of spaced-apart and angled front struts 23 in the form of turnbuckles. The turnbuckle struts 23 each comprise a lower left-handed, threaded rod 24 mounted in support member 21 and an upper right-handed, threaded member 25 mounted in upper support member 22, on both of which is received an internally-threaded, cylindrical sleeve 26. Upon turning, threaded, cylindrical sleeve 26 will either increase or decrease the effective length of the turnbuckle and, in turn, the spacing between support members 21 and 22, the purpose of which will be described in greater detail hereinafter.

As seen best in FIGS. 2 and 3, the rearwardly-disposed terminal end portions of the support members 21 and 22 are joined together via a pair of generally L-shaped, interiorly-padded rear struts 27 each composed of a back plate 27' and a side plate 27''. The struts 27 are preferably rearwardly tilted approximately 65 degrees so that the upper support member 22 is similarly angularly and rearwardly offset from the lower support member 21. A pair of spaced apart rear straps 28, in the form of PVC tubing, interconnects the rear struts 27. The PVC plastic tubing preferably has an outside diameter of 9/16 of an inch, an inside diameter of 7/16 of an inch, and walls of approximately 1/16 of an inch, and is approximately 16 inches long. The tube straps 28 are provided with a series of spaced-apart adjustment holes 29 along their terminal ends by which the same can be releasably fastened to the either the back plate 27' or side plate 27'' of the rear struts 27 via a threaded pins 30 mounted on the rear struts 27 and corresponding nuts 31; preferably the lower strap would be affixed to the back plate 27' (not shown for purposes of clarity).

Alternatively, the rear strap could comprise a belt having VELCRO ® hook-like fasteners (not shown), which in turn, could mate with the VELCRO ® loop-type fasteners 32 mounted on rear struts 27, depending upon the degree of support and immobility required by the doctor for the particular patient (i.e., the plastic tube straps 28 providing a firmer, more rigid, yet comfortable support for the patient's head, as opposed to a VELCRO ® strap). In this regard, it should be noted that the top strap 28 is positioned over the top of the L-shaped, rear struts 27 (and above stem 66 and nut 67, which serve as abutment stops) and, in this position, will provide a firm support for the rear of the patient's head.

As also shown, the cervical collar can be further affixed to the torso of the patient via additional straps 33 affixed to the rear struts 27, for example, via threaded pins 34 and threaded bores 35, the latter of which is provided in the rear struts. The lower portion of the straps could be attached to a chest support assembly, such as that shown in U.S. Pat. No. 3,724,452, or they could be drawn underneath the patient's arms in a crisscross fashion and back to the front of the collar, wherein there could be reattached via VELCRO ® fastening means 36 to the lower support member 21.

As shown best in FIGS. 1 and 4–7, the chin support assembly 40 includes a generally horizontally-disposed pivot support plate 41 supported above the upper support member 22 and mounted on the threaded rods 25 of struts 23, which extend through support member 22. A generally horizontally-disposed chin support plate 42 is connected to a pair of arcuate, lateral end walls 43, which in turn, are pivotably mounted on the pivot support plate 41 via hinge or pivot element 44. The lateral end walls 43 also have a series of spaced-apart adjustment holes 45 by which the doctor can adjust the pivot angle of the chin support plate 42 relative to the pivot support plate 41. The angular position of two plates is set by the provision of a set screw 46 receivable through one of the adjustment holes 45 and receivable in a bore (not shown) provided in the end wall of the pivot support plate 41. In addition, a pair of threaded rods 46 are provided, which are receivable in angled threaded bores of both of the pivot support plate 41 and the chin support plate 42, so as to securely fix the pivot angle between the support plates and provide additional rigidity and immobility thereto. The rods 46 can also be individually adjusted to effectively tilt the chin support plate 42 laterally, if desired.

The chin support plate 42 has a plastic, generally cylindrical, horizontally-disposed chin support bar 59 mounted thereon, on which the wearer's chin may rest. In addition, the chin support plate 42 and the lateral end members 43 are provided with relatively soft, molded foam cushioning means, or chin support means 47, disposed rearwardly of the chin support bar 59, on which the chin of the wearer may also rest comfortably (see, FIGS. 1 and 7). As can be appreciated, the chin rest 47 can be modified to generally conform to the profile of the wearer's chin.

As seen in FIGS. 1–3 and 5, the lateral end walls 43 are preferably further connected to the rear struts 27 via a pair of adjustable-length side support braces or struts 48, one end of each of which is coupled to opposite lateral end wall 43, via pivot and length adjustment means, and to the rear strut 27, via a threaded pin 66 and nut 67. The adjustable-length side brace 48 includes a generally L-shaped support lug 49 having a threaded bore which, in turn, receives a threaded rod 50 which is threadably affixed to a U-shaped yoke 51, the arms of which are pivotably connected to one end of the side support brace 48 via a generally vertically-oriented pivot pin 52. The threaded rod 50 can be turned to adjust the effective length of the side brace to either lengthen or shorten the same and is fixed in place by nuts 54. The hinge or pivot support of the side support brace 48 provides for greater adaptability and adjustment to conform to the particular shape of the head of the user.

The collar optionally includes a head support assembly 60 which includes a pair of rectangular, padded head support members 61 for engaging and supporting the ossiput of the wearer on the support brace 20 and the chin support 40. Two pairs of adjustable-length head support braces or struts 62 constructed in a similar fashion to that of the side support braces 48 are provided to mount the head support members 61, 62. One pair of the head support struts are connected to one head support member 61, and the other pair is connected to the opposite head support member 61.

In particular, each of the struts 62 of each pair includes a lower end having a series of spaced-apart, adjustable holes 63 formed therethrough by which one of the struts of the pair can be attached to one of the lateral end walls 43 and chin support means 47 via a threaded stem 64 (see FIG. 5) and nut 65 and the other of the struts can be attached to one of the rear struts 27 via a threaded stem 66 and nut 67. The upper ends of each of the struts 62 is pivotably attached via a generally horizontally-disposed pivot pin 68 to the arms of a U-shaped yoke 69 which, in turn, is connected via a threaded stem 70 to an L-shaped leg 71 attached to one of the head support members 61. The threaded stem 71 can be adjusted by turning it to lengthen or shorten, respectively, the effective length of the head support strut 62, and it can be locked in place via nuts 72. Here again, the angle and length adjustment enables a more individual and proper fit for the particular wearer.

The head support assembly further includes a releasable strap 73, which interconnects the pair of head support members 61 to provide further rigidity to the patient's head. The outer face of the head support members can include VELCRO ® loop fasteners 74, and the ends of the strap would be similarly provided with the complementary VELCRO ® hook fasteners 75 for releasible attachment thereto.

Most desirably, the various components of the present cervical collar are fabricated from X-ray transmissive materials, such as plastic. It is also preferable that the plastic employed be transparent or translucent so that it will not be noticeable for aesthetic reasons.

As can be appreciated, the present invention provides a widely versatile cervical collar which can be easily and universally adjusted to support the particular size and shape head of the wearer via its various adjustment features, which allow forward, rearward, upward, downward and angular adjustment to accommodate differently dimensioned patients' heads. In addition, the use of plastic tubing for the support members and straps surprisingly provide a highly effective combination of rigidity and resiliency to provide a comfortable, yet medically proper, fit, which immobilizes the patient's head and neck.

Accordingly, while only one embodiment of the present invention have been shown and described, it is to be understood that many changes and modifications may be made thereunto without departing from the spirit and scope of the invention.

What is claimed is:

1. A cervical collar, comprising:
 a generally annular support brace which, in use, is receivable about and circumferentially surrounds a wearer's neck and is generally supportable on the wearer's shoulders and upper torso, said support brace including a pair of vertically-spaced-apart, interconnected and generally horizontally-disposed, arcuate, upper and lower support members, each composed of a plastic resilient tube, and each having a front central portion and rear opposite terminal end portions which, in use, are disposed generally adjacent to the front and rear of the wearer's neck, respectively, said support brace including a pair of generally vertically-extending rear struts interconnecting the rear terminal end portions of said support members and adjustable and releasable rear strap means for joining said terminal end portions of said support members together via said rear struts, said strap means including at least one strap disposed over and generally above said terminal end portions of said upper support member so as to be positioned to support the back of the head of the wearer and a second rear strap spaced below said at least one strap;
 chin support means for engaging and supporting the chin of the wearer; and
 mounting means for adjustably mounting said chin support means on said support brace.

2. The collar of claim 1, wherein said plastic tube is made of PVC.

3. The collar of claim 1, wherein said strap means comprises at least one plastic tube.

4. The collar of claim 3, wherein said plastic tube has a plurality of spaced-apart adjustment holes formed therethrough and said strap means includes releasable fasteners for joining said tubes via said adjustment holes to said rear struts.

5. The collar of claim 1, wherein said support brace includes a pair of generally vertically extending, spaced-apart front struts interconnecting said front central portions of said support members.

6. The collar of claim 5, wherein said front struts each comprise a turnbuckle for adjusting the spacing between said support members.

7. The collar of claim 1, wherein said mounting means includes means for pivotably supporting said chin support means.

8. The collar of claim 7, wherein said means for pivotably supporting said chin support means includes a generally horizontally-disposed pivot support plate adjustably mounted on said collar support, said chin support means being pivotably mounted on said pivot support plate.

9. The collar of claim 8, wherein said chin support means includes a generally horizontally-disposed chin support plate and a pair of generally vertically-disposed lateral end walls, each joined to an opposite lateral end of said chin support plate, said lateral end walls including pivot means for pivotably mounting said lateral end walls on said pivot support plate and releasable locking means for locking said lateral end walls and, in turn, said chin support plate at a predetermined and adjustable pivot angle with respect to said pivot support plate.

10. The collar of claim 9, wherein said lateral end walls have a plurality of spaced-apart holes formed therethrough and said pivot support plate has a pair of opposite lateral side walls, each with a threaded throughbore formed therein and wherein said releasable locking means includes a pair of threaded locking pins each of which is releasably received in one of said holes and throughbores so as to lock said lateral end walls and, in turn, said chin support plate, at a fixed pivot angle with respect to said pivot support plate.

11. The collar of claim 10, wherein said chin support plate and said lateral end walls have resilient chin rest means mounted thereon configured to generally conform to and provide direct support for the wearer's chin.

12. The collar of claim 10, wherein said mounting means includes adjustable-length side support braces, one end of each of which is releasably attached to an opposite lateral end wall of said chin support means, and the other end of each of which is releasably attached to an opposite rear strut of said support brace.

13. The collar of claim 12, wherein one end of each of said side support braces is connected to opposite ones of said lateral end walls via pivot means.

14. The collar of claim 1, additionally including a pair of head support members for engaging and supporting the occiput of the wearer and mounting means for adjustably mounting the head support members on at least one of said support brace and said chin support means.

15. The collar of claim 14, wherein said mounting means comprises two pairs of adjustable-length head support struts, one pair end of each of which is connected to an opposite head support member and to an opposite one of said rear support struts and said lateral end walls.

16. The collar of claim 15, wherein said adjustable-length head support struts are connected to said head support members via pivot means.

17. The collar of claim 15, additionally including releasable strap means connecting said pair of head support means.

18. The collar of claim 1, additionally including strap means for connecting said support brace to the wearer's torso.

19. The collar of claim 1, wherein said annular support brace, chin support means and mounting means are fabricated from X-ray transmissive materials.

20. A cervical collar, comprising:
a generally annular support brace which, in use, is receivable about and circumferentially surrounds a wearer's neck and is generally supportable on the wearer's shoulders and upper torso, said support brace including a pair of vertically-spaced-apart, interconnected and generally horizontally-disposed, arcuate, upper and lower support members each having a front central portion and rear opposite terminal end portions which in use, are disposed generally adjacent to the front and rear of the wearer's neck, respectively, and adjustable and releasable rear strap means for joining said terminal end portions of said support members together;
chin support means for engaging and supporting the chin of the wearer said mounting means including means for pivotably supporting said chin support means, said means for pivotably supporting said chin support means including a generally horizontally-disposed pivot support plate adjustably mounted on said collar support, said chin support means being pivotably mounted on said pivot support plate, wherein said chin support means includes a generally horizontally-disposed chin support plate and a pair of generally vertically-disposed lateral end walls, each joined to an opposite lateral end of said chin support plate, said lateral end walls including pivot means for pivotably mounting said lateral end walls on said pivot support plate and releasable locking means for locking said lateral end walls and, in turn, said chin support plate at a predetermined and adjustable pivot angle with respect to said pivot support plate; and
mounting means for adjustably mounting said chin support means on said support brace.

21. A cervical collar, comprising:
a generally annular support brace which, in use, is receivable about and circumferentially surrounds a wearer's neck and is generally supportable on the wearer's shoulders and upper torso, said support brace including a pair of vertically-spaced-apart, interconnected and generally horizontally-disposed, arcuate, upper and lower support members each having a front central portion and rear opposite terminal end portions which in use, are disposed generally adjacent to the front and rear of the wearer's neck, respectively, and adjustable and releasable rear strap means for joining said terminal end portions of said support members together;
chin support means for engaging and supporting the chin of the wearer;
a pair of head support members for engaging and supporting the occiput of the wearer and mounting means for adjustably mounting the head support members on at least one if said support brace and said chin support means; and
mounting means for adjustably mounting said chin support means on said support brace, said mounting means comprises two pairs of adjustable-length head support struts, one pair end of each of which is connected to an opposite head support member and to an opposite one of said rear support struts and said lateral end walls.

* * * * *